United States Patent [19]

Keck et al.

[11] 4,006,246
[45] Feb. 1, 1977

[54] PHARMACEUTICAL COMPOSITIONS CONTAINING AN AMINOBENZYL-AMINE AND METHOD OF USE

[75] Inventors: Johannes Keck, Biberach an der Riss; Klaus-Reinhold Noll, Warthausen-Oberhofen; Helmut Pieper, Biberach an der Riss; Gerd Kruger, Biberach an der Riss; Sigfrid Puschmann, Biberach an der Riss, all of Germany

[73] Assignee: Boehringer Ingelheim GmbH, Ingelheim am Rhein, Germany

[22] Filed: Jan. 15, 1976

[21] Appl. No.: 649,481

Related U.S. Application Data

[62] Division of Ser. No. 458,099, April 5, 1974, Pat. No. 3,950,393.

[30] Foreign Application Priority Data

Apr. 13, 1973  Germany ........................... 2318636
Jan. 23, 1974  Germany ........................... 2402989

[52] U.S. Cl. .............................. 424/309; 424/319; 424/330
[51] Int. Cl.² ................. A61K 31/19; A61K 31/24; A61K 31/135
[58] Field of Search ................... 424/330, 309, 319

[56] References Cited
OTHER PUBLICATIONS

Helv. Chim. Acta 48, 259–274 (1965).

Primary Examiner—Stanley J. Friedman
Attorney, Agent, or Firm—Hammond & Littell

[57] ABSTRACT

Pharmaceutical dosage unit compositions containing as an active ingredient a compound of the formula

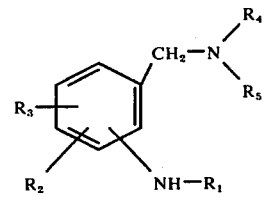

wherein
$R_1$ is hydrogen, lower alkanoyl, benzoyl or halobenzoyl,
$R_2$ is hydrogen, chlorine or bromine,
$R_3$ is carboxyl or lower carbalkoxy, and
$R_4$ and $R_5$ are each hydrogen, alkyl of 1 to 5 carbon atoms, mono- or di-hydroxy-(alkyl of 1 to 5 carbon atoms), alkenyl or 2 to 4 carbon atoms, cycloalkyl of 5 to 7 carbon atoms, mono- or di-hydroxy-(cycloalkyl of 5 to 7 carbon atoms) or benzyl, or a non-toxic, pharmacologically acceptable acid addition salt thereof; and a method of using the same as anti-ulcerogenics, secretolytics, antitussives, and stimulants of the production of the surfactant or antiatelectasis factor of the alveoli.

6 Claims, No Drawings

PHARMACEUTICAL COMPOSITIONS CONTAINING AN AMINOBENZYL-AMINE AND METHOD OF USE

This is a division of copending application Ser. No. 458,099 filed Apr. 5, 1974, now U.S. Pat. No. 3,950,393, granted Apr. 13, 1976.

This invention relates to novel pharmaceutical compositions containing an aminobenzyl-amine or a non-toxic acid addition salt thereof, as well as to a method of using the same as anti-ulcerogenics, secretolytics, antitussives and stimulants of the production of the surfactant or antiatelectasis factor of the alveoli.

More particularly, the present invention relates to novel pharmaceutical dosage unit compositions containing as an active ingredient a compound of the formula

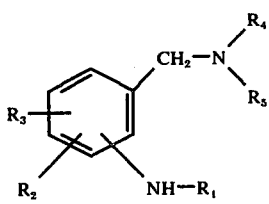

wherein
  $R_1$ is hydrogen, lower alkanoyl, benzoyl or halobenzoyl,
  $R_2$ is hydrogen, chlorine or bromine,
  $R_3$ is carboxyl or lower carbalkoxy, and
  $R_4$ and $R_5$ are each hydrogen, alkyl of 1 to 5 carbon atoms, mono- or di-hydroxy-(alkyl of 1 to 5 carbon atoms), alkenyl of 2 to 4 carbon atoms, cycloalkyl of 5 to 7 carbon atoms, mono- or di-hydroxy-(cycloalkyl of 5 to 7 carbon atoms) or benzyl,
or a non-toxic, pharmacologically acceptable acid addition salt thereof.

The compounds embraced by formula I may be prepared by various methods involving well known chemical synthesis principles, among which the following have proved to be most convenient and efficient:

Method A

By reacting a compound of the formula

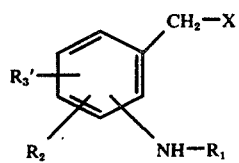

wherein
  $R_1$ and $R_2$ have the same meanings as in formula I,
  X is chlorine, bromine, iodine, hydroxyl, acyloxy, sulfonyloxy, alkoxy, aryloxy, aralkoxy, trialkylammonium or pyridinium, and
  $R_3'$ has the meanings defined for $R_3$ in formula I or $-CH_2-X$, where X has the meanings defined above,
with an amine of the formula

wherein $R_4$ and $R_5$ have the same meanings as in formula I.

Particularly preferred embodiments of substituent X in formula II are chlorine, bromine, hydroxyl, acetoxy, butyryloxy, benzoyloxy, methylsulfonyloxy, p-toluenesulfonyloxy, methoxy, ethoxy, phenoxy, trimethylammonium and pyrridinium. Thus, X may be any group which, starting from a compound of the formula II, easily severs from the molecule and enables the intermediate formation of a benzyl cation.

The reaction is advantageously performed in a solvent medium, such as carbon tetrachloride, chloroform, methanol, tetrahydrofuran, benzene, toluene, ether, dioxane, tetrahydronaphthalene or an excess of the amine of the formula III, and, depending upon the reactivity of substituent X, at temperatures between $-70°$ and $+200°$ C. However, the reaction will also proceed without the presence of a solvent medium.

In those instances where the reaction is performed with a compound of the formula II wherein X is hydroxyl and the 2-position of the phenyl ring is occupied by an acylamino substituent, the acyl moiety of this substituent can be split off during the reaction.

If X in formula II is arylsulfonyloxy, such as p-toluene-sulfonyloxy, the reaction is preferably performed at a temperature between $-70°$ and $+50°$ C in a solvent medium, such as an aliphatic or cyclic ether.

If X in formula II is halogen, the reaction is preferably performed at temperatures between $0°$ and $150°$ C, especially at the boiling point of the particular solvent medium which is employed, and advantageously in the presence of a hydrogen halide-binding agent, such as an inorganic base, especially sodium carbonate or sodium hydroxide; an ion exchanger; a tertiary organic base, especially triethylamine or pyridine; or an excess of the particular amine of the formula III. In this case, if a tertiary organic base is used as the hydrogen halide-binding agent, it may simultaneously serve as the solvent medium for the reaction.

If X in formula II is acyloxy, such as acetoxy or benzoyloxy, alkoxy, aryloxy or aralkoxy, the reaction is optionally carried out in the presence of an acid catalyst, such as ammonium chloride, acid aluminum oxide or sulfuric acid, and preferably at temperatures between $0°$ and $200°$ C.

If X in formula II is hydroxyl, the reaction is optionally carried out in the presence of an acid catalyst, such as sulfuric acid, hydrobromic acid, p-toluene-sulfonic acid or a lower alkanoic acid, such as propionic acid or butyric acid; it may optionally also be performed in the presence of an alkaline catalyst, such as potassium hydroxide, magnesium oxide or sodium amide. In either case the preferred reaction temperature range is from $120°$ to $180°$ C, and the reaction may be performed in the presence or absence of a solvent medium.

Finally, if X in formula II is trialkylammonium or pyridinium, the reaction is preferably performed in an excess of the particular amine of the formula III which serves as the solvent medium, and at a temperature between 120° and 180° C. However, the reaction also proceeds in the absence of a solvent medium.

Method B

For the preparation of a compound of the formula I wherein $R_2$ is chlorine or bromine, and $R_4$ and/or $R_5$ have the meanings previously defined, except alkenyl of 2 to 4 carbon atoms, by halogenating a compound of the formula

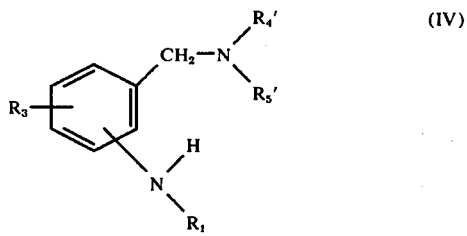

wherein
$R_1$ and $R_3$ have the same meanings as in formula I, and
$R_4'$ and $R_5'$ have the same meanings as $R_4$ and $R_5$ in formula I, except alkenyl of 2 to 4 carbon atoms.

The halogenation is effected with a conventional halogenating agent, such as chlorine, bromine, bromo tribromophenate or phenyl iodide dichloride, preferably in a solvent medium, such as 50–100% acetic acid, methylene chloride or tetrahydrofuran, in the presence of a tertiary organic base, such as triethylamine or pyridine, and advantageously at a temperature between $-20°$ and $+50°$ C. 1 mol of halogenating agent or a slight excess thereover is provided per mol of compound IV; the latter may be employed in the form of its free base or also in the form of an acid addition salt, such as its mono-, di- or trihydrochloride. If the end product obtained by this method is a hydrohalic acid addition salt of a compound of the formula I, the same may be isolated as such or further purified by way of its free base.

Method C

For the preparation of a compound of the formula I wherein $R_1$ and/or $R_4$ are hydrogen, by splitting off one or two protective groups from a compound of the formula

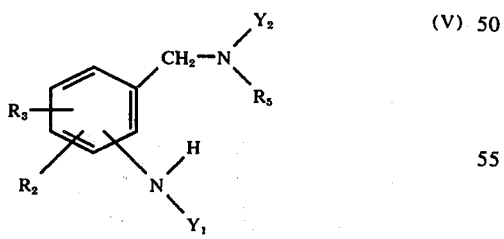

wherein
$R_2$, $R_3$ and $R_5$ have the same meanings as in formula I,
$Y_1$ has the meanings defined above for $R_1$ or is an amino-protective group which can be split off by hydrolysis or hydrogenation, and
$Y_2$ has the meanings defined above for $R_4$ or is an amino-protective group which can be split off by hydrolysis or hydrogenation, provided, however, that at least one of $Y_1$ and $Y_2$ must be an amino-protective group.

For instance, if $Y_1$ and/or $Y_2$ are acyl, such as acetyl, benzoyl or p-toluenesulfonyl, trimethylsilyl or tetrahydropyranyl-(2), the removal of these protective groups is effected by hydrolysis in the presence of a solvent, such as with ethanolic hydrochloric acid or aqueous-ethanolic sodium hydroxide, at temperatures between 20° and 150° C, but preferably at the boiling point of the particular solvent which is used. If $R_3$ in formula V is cyano, carbalkoxy or carbamoyl, these substituents can be simultaneously hydrolized into carboxyl by this method.

On the other hand, if $Y_1$ and/or $Y_2$ are benzyloxycarbonyl or benzyl, for example, the removal of these protective groups is effected by hydrogenation, such as with hydrogen in the presence of palladium as a catalyst, for example, and preferably at room temperature in the presence of a solvent, such as methanol, methanol/water or methanol/hydrochloric acid. If $R_4$ and/or $R_5$ in formula V are alkenyl of 2 to 4 carbon atoms, these are simultaneously reduced to alkyl.

Method D

For the preparation of a compound of the formula I wherein $R_3$ is carboxyl, by hydrolizing a compound of the formula

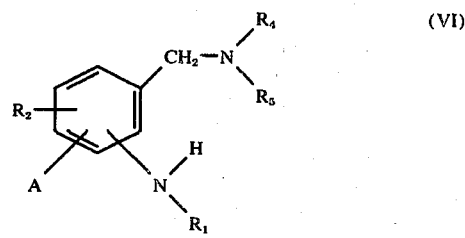

wherein
$R_1$, $R_2$, $R_4$ and $R_5$ have the same meanings as in formula I, and
A is a functional derivative of carboxy, such as amido, imido, alkoxycarbonyl or cyano.

The hydrolysis is advantageously performed in a solvent, such as methanol, ethanol, methanol/water, ethanol/water, dioxane/water or water, in the presence of an acid, such as trifluoroacetic acid, hydrochloric acid or sulfuric acid, or in the presence of a base, such as sodium hydroxide, and at temperatures between 50° and 150° C, but preferably at the boiling point of the particular solvent which is used.

If $R_1$ in formula VI is acyl, this substituent is simultaneously split off during the hydrolysis.

If the above methods yield a compound of the formula I wherein $R_1$ is hydrogen and $R_2$, $R_3$, $R_4$ and $R_5$ have the meanings previously defined except substituents containing a reactive hydrogen atom, such a compound may, if desired, be subsequently acylated. The acylation is advantageously carried out with a reactive derivative of an acid, such as an acid halide, acid anhydride or mixed acid anhydride, or in the presence of a dehydrating agent, such as N,N'-dicyclohexyl-carbodiimide.

The starting compounds for methods A to D are either known compounds and/or may be prepared by known processes.

For example, a compound of the formula II may be obtained by reacting a corresponding toluene derivative with N-bromo-succinimide or with halogen under ultraviolet radiation; or also by reacting a corresponding benzyl alcohol with thionyl chloride; or by reacting a corresponding benzyl halide with an alkali metal salt of a carboxylic acid, an alkali metal alcoholate or alkali metal phenolate; or by halogenating a corresponding benzylammonium salt.

The benzylamines of the formulas IV, V and VI may be obtained by reacting a corresponding halide with a corresponding amine.

The compounds embraced by formula I are organic bases and therefore form acid addition salts with inorganic or organic acids. Examples of non-toxic, pharmacologically acceptable acid addition salts are those formed with hydrochloric acid, hydrobromic acid, sulfuric acid, phosphoric acid, lactic acid, citric acid, tartaric acid, maleic acid, fumaric acid, 8-chlorotheophylline or the like.

The following examples illustrate the present invention and will enable others skilled in the art to understand it more completely. It should be understood, however, that the invention is not limited solely to the particular examples given below.

EXAMPLE 1

N-Ethyl-2-amino-3-bromo-5-carboxy-N-cyclohexyl-benzylamine hydrochloride by method D 13 gm of N-ethyl-2-amino-3-bromo-5-carbethoxy-N-cyclohexyl-benzylamine were boiled with 100 ml of 6 N hydrochloric acid for 1 hour. Subsequently, the supernatant liquid was decanted from the oily phase which had formed at the bottom, and the solution was evaporated to dryness. The residue was recrystallized from methanol, yielding N-ethyl-2-amino-3-bromo-5-carboxy-N-cyclohexyl-benzylamine hydrochloride, m.p. 227°–229° C.

EXAMPLE 2

2-Acetamino-3-bromo-5-carbethoxy-N,N-diethyl-benzylamine and its hydrochloride 1 gm of 2-amino-3-bromo-5-carbethoxy-N,N-diethyl-benzylamine were dissolved in 2 ml of acetylchloride, and the solution was heated at 50° C for 1 hour. The excess acetylchloride was evaporated in vacuo, the residue was distributed between cold dilute ammonia and chloroform, the chloroform solution was evaporated, the residue was purified by chromatography on silica gel (elution agent: ethyl acetate), the evaporation residue of the eluate was dissolved in isopropanol, and 2-acetamino-3-bromo-5-carbethoxy-N,N-diethylbenzylamine hydrochloride, m.p. 190°–194° C, was caused to crystallize out by addition of isopropanolic hydrochloric acid and ether.

EXAMPLE 3

2-Acetamino-5-carbethoxy-N,N-diethyl-benzylamine by method A 30 gm of 2-acetamino-5-carbethoxy-benzyl bromide were dissolved in a mixture of 400 ml of chloroform and 100 ml of ethanol, and the solution was refluxed with 22 gm of diethylamine for 1 hour. Thereafter, the reaction solution was cooled, then evaporated in vacuo, the residue was distributed between a mixture of dilute ammonia and chloroform, and the chloroform phase was dried over sodium sulfate and evaporated in vacuo. The residue was purified by chromatography on silicagel (elution agent: ethyl acetate) and recrystallized from ethanol, yielding 2-acetamino-5-carbethoxy-N,N-diethyl-benzylamine, m.p. 57°–59° C.

EXAMPLE 4

2-Amino-3-bromo-5-carbethoxy-N,N-diethyl-benzylamine and its hydrochloride by method B 80 gm of 2-amino-5-carbethoxy-N,N-diethyl-benzylamine were dissolved in a mixture of 300 ml of glacial acetic acid and 30 ml of water, and the solution was admixed dropwise, while stirring, with a solution of 40 gm of bromine in 40 ml of glacial acetic acid at room temperature, and the mixture was allowed to stand for 1 hour. Thereafter, it was poured over ice, made alkaline with ammonia and extracted with chloroform. The combined chloroform extracts were evaporated to dryness in vacuo, and the residue was purified by chromatography on silicagel (elution agent: ethyl acetate) and converted with isopropanolic hydrochloric acid into 2-amino-3-bromo-5-carbethoxy-N,N-diethyl-benzylamine hydrochloride, which was recrystallized from ethanol, whereupon it had a melting point of 165°–168° C.

EXAMPLE 5

2-Amino-5-carbethoxy-N,N-diethyl-benzylamine and its hydrochloride by method C 19 gm of 2-acetamino-5-carbethoxy-N,N-diethyl-benzylamine were dissolved in 100 ml of ethanol, and after addition of 60 ml of concentrated hydrochloric acid the mixture was refluxed for 1 hour. Thereafter the mixture was poured over ice, made alkaline with ammonia and extracted three times with chloroform. The combined chloroform extracts were dried over sodium sulfate and evaporated in vacuo, and the residue was purified by chromatography on silicagel (elution agent: ethyl acetate); by addition of isopropanolic hydrochloric acid, 2-amino-5-carbethoxy-N,N-diethyl-benzylamine hydrochloride was obtained, which was recrystallized from ethanol and then had a melting point of 138°–142° C.

EXAMPLE 6

2-Amino-5-carboxy-N-cyclohexyl-N-methyl-benzylamine by method D

A mixture of 21 gm of 2-acetamino-5-carbethoxy-N-cyclohexyl-N-methyl-benzylamine, 100 ml of ethanol, 90 ml of water and 60 ml of concentrated hydrochloric acid was refluxed for 1 hour. Thereafter, the reaction solution was cooled, poured over ice, made alkaline with ammonia and extracted three times with chloroform. The aqueous alkaline phase was evaporated to dryness in vacuo, the residue was thoroughly stirred with ethanol, and the mixture was filtered. The filtrate was evaporated to dryness in vacuo, and the residue was recrystallized from ethanol, yielding 2-amino-5-carboxy-N-cyclohexyl-N-methyl-benzylamine, m.p. 200°–205° C.

EXAMPLE 7

2-Amino-N-tert.butyl-5-carbethoxy-benzylamine by method D 3.4 gm of 2-amino-N-benzyl-N-tert.butyl-5-carbethoxy-benzylamine were dissolved in 50 ml of ethanol.

Ethanolic hydrochloric acid was added to the solution until a pH of about 2 was reached. The solution was then hydrogenated in the presence of palladized (10%) charcoal. After absorption of 1 mol of hydrogen, the hydrogenation was terminated, the catalyst was filtered off, the filtrate was evaporated to dryness in vacuo, and the residue was distributed between a mixture of dilute ammonia and chloroform. The chloroform phase was dried and evaporated to dryness, and the residue was recrystallized from ethanol, yielding 2-amino-N-tert.butyl-5-carbethoxy-benzylamine, m.p. 77°–79° C.

EXAMPLE 8

2-Acetamino-N-tert.butyl-5-carbethoxy-benzylamine, m.p. 136°–139° C, was prepared from 2-acetamino-5-carbethoxybenzyl bromide and tert.butylamine analogous to Example 3.

EXAMPLE 9

2-Amino-N-tert.butyl-5-carbethoxy-benzylamine, m.p. 77°–79° C, was prepared by hydrolysis of 2-acetamino-N-tert.butyl-5-carbethoxy-benzylamine in ethanolic hydrochloric acid analogous to Example 5.

EXAMPLE 10

2-Amino-3-bromo-N-tert.butyl-5-carbethoxy-benzylamine, m.p. 78°–81° C, was prepared from 2-amino-N-tert.butyl-5-carbethoxy-benzylamine and bromine analogous to Example 4.

EXAMPLE 11

2-Acetamino-5-carbethoxy-N-cyclohexyl-N-methyl-benzylamine, m.p. 71°–74° C, was prepared from 2-acetamino-5-carbethoxybenzyl bromide and N-methyl-cyclohexylamine analogous to Example 3.

EXAMPLE 12

2-Amino-5-carbethoxy-N-cyclohexyl-N-methyl-benzylamine and its hydrochloride, m.p. 160°–170° C, was prepared by hydrolysis of 2-acetamino-5-carbethoxy-N-cyclohexyl-N-methylbenzylamine in ethanolic hydrochloric acid analogous to Example 5.

EXAMPLE 13

2-Amino-3-bromo-5-carbethoxy-N-cyclohexyl-N-methyl-benzylamine and its hydrochloride, m.p. 212°–215° C, were prepared from 2-amino-5-carbethoxy-N-cyclohexyl-N-methyl-benzylamine and bromine analogous to Example 4.

EXAMPLE 14

2-Amino-5-carbethoxy-3chloro-N-cyclohexyl-N-methyl-benzylamine and its hydrochloride, m.p. 207°–209° C, were prepared from 2-amino-5-carbethoxy-N-cyclohexyl-N-methyl-benzylamine and chlorine analogous to Example 4.

EXAMPLE 15

2-Acetamino-3-bromo-5-carbethoxy-N-cyclohexyl-N-methylbenzylamine and its hydrochloride, m.p. 220°–223° C, were prepared from 2-amino-3-bromo-5-carbethoxy-N-cyclohexyl-N-methyl-benzylamine and acetylchloride analogous to Example 2.

EXAMPLE 16

2-Acetamino-N-ethyl-5-carbethoxy-N-cyclohexyl-benzylamine, m.p. 92°–95° C, was prepared from 2-acetamino-5-carbethoxybenzyl bromide and N-ethyl-cyclohexylamine analogous to Example 3.

EXAMPLE 17

N-Ethyl-2-amino-5-carbethoxy-N-cyclohexyl-benzylamine and its dihydrochloride, m.p. 188°–194° C, were prepared by hydrolysis from 2-acetamino-N-ethyl-5-carbethoxy-N-cyclohexyl-benzylamine in ethanolic hydrochloric acid analogous to Example 5.

EXAMPLE 18

N-Ethyl-2-amino-3-bromo-5-carbethoxy-N-cyclohexyl-benzylamine, m.p. 66°–68° C, was prepared from N-ethyl-2-amino-5-carbethoxy-N-cyclohexylbenzylamine and bromine analogous to Example 4.

EXAMPLE 19

N-Ethyl-2-amino-5-carbethoxy-3-chloro-N-cyclohexyl-benzylamine and its hydrochloride, m.p. 165°–170° C, were prepared from N-ethyl-2-amino-5-carbethoxy-N-cyclohexyl-benzylamine and chlorine analogous to Example 4.

EXAMPLE 20

2-Amino-5-carboxy-N,N-diethyl-benzylamine and its hydrochloride, m.p. 194°–198° C, were prepared by hydrolysis of 2-amino-5-carbethoxy-N,N-diethyl-benzylamine in hydrochloric acid analogous to Example 1.

EXAMPLE 21

2-Amino-3-bromo-5-carboxy-N,N-diethyl-benzylamine and its hydrochloride, m.p. 233°–234° C (decomp.), were prepared by hydrolysis of 2-amino-3-bromo-5-carbethoxy-N,N-diethyl-benzylamine in hydrochloric acid analogous to Example 1.

EXAMPLE 22

2-Amino-N-tert.butyl-5-carboxy-benzylamine and its hydrochloride, m.p. 220°–230° C, were prepared by hydrolysis of 2-acetamino-N-tert.butyl-5-carbethoxy-benzylamine in hydrochloric acid analogous to Example 6.

EXAMPLE 23

2-Amino-3-bromo-N-tert.butyl-5-carboxy-benzylamine and its hydrochloride, m.p. 270°–280° C (decomp.), were prepared by hydrolysis of 2-amino-3-bromo-N-tert.butyl-5-carbethoxy-benzylamine in hydrochloric acid analogous to Example 1.

EXAMPLE 24

2-Acetamino-5-carboxy-N-cyclohexyl-N-methyl-benzylamine and its hydrochloride, m.p. 228°–232° C, were prepared from 2-amino-5-carboxy-N-cyclohexyl-N-methyl-benzylamine and acetylchloride analogous to Example 2.

EXAMPLE 25

2-Amino-3-bromo-5-carboxy-N-cyclohexyl-N-methyl-benzylamine and its hydrochloride, m.p. 230°–240° C, were prepared by hydrolysis of 2-amino-3-bromo-5-carbethoxy-N-cyclohexyl-N-methyl-benzylamine in hydrochloric acid analogous to Example 1.

EXAMPLE 26

N-Ethyl-2-amino-5-carboxy-N-cyclohexyl-benzylamine and its dihydrochloride, m.p. 175°–181° C, were prepared by hydrolysis of N-ethyl-2-amino-5-carbethoxy-N-cyclohexyl-benzylamine in hydrochloric acid analogous to Example 1.

EXAMPLE 27

N-Ethyl-2-amino-5-carboxy-3-chloro-N-cyclohexyl-benzylamine and its hydrochloride, m.p. 228°–232° C, were prepared by hydrolysis of N-ethyl-2-amino-5-carbethoxy-3-chloro-N-cyclohexyl-benzylamine in hydrochloric acid analogous to Example 1.

EXAMPLE 28

2-Benzoylamino-3-bromo-5-carbethoxy-N,N-diethyl-benzylamine and its hydrochloride, m.p. 220°–222° C, were prepared from 2-amino-3-bromo-5-carbethoxy-N,N-diethyl-benzylamine and benzoyl chloride in benzene analogous to Example 2.

EXAMPLE 29

3-Bromo-5-carbethoxy-2-(4′-chloro-benzoylamino)-N,N-diethylbenzylamine and its hydrochloride, m.p. 187°–193° C, were prepared from 2-amino-3-bromo-5-carbethoxy-N,N-diethyl-benzylamine and 4-chloro-benzoyl chloride in benzene analogous to Example 2.

EXAMPLE 30

2-Acetamino-5-carbomethoxy-N,N-diethylbenzylamine and its hydrochloride by method A 3.4 gm of 2-acetamino-5-carbomethoxy-benzyl bromide were dissolved in 125 ml of chloroform and after addition of 35 gm of diethylamine the mixture was allowed to stand for 15 minutes. The mixture was then evaporated to dryness in vacuo, the residue was dissolved in chloroform, the chloroform solution was extracted with dilute hydrochloric acid, and the aqueous phase was made alkaline with ammonia and again extracted with chloroform. This chloroform extract was dried over sodium sulfate and evaporated in vacuo. The residue, consisting of the free base 2-acetamino-5-carbomethoxy-N,N-diethyl-benzylamine (m.p. 77°–80° C), was converted into its hydrochloride, m.p. 213°–214° C, with methanolic hydrochloric acid.

EXAMPLE 31

2-Amino-3-bromo-5-carbomethoxy-N,N-diethyl-benzylamine and its hydrochloride by method B A solution of 1.1 gm of bromine in 2 ml of acetic acid was added dropwise, while stirring at room temperature, to a solution of 1.6 gm of 2-amino-5-carbomethoxy-N,N-diethyl-benzylamine in a mixture of 27 ml of acetic acid and 3 ml of water. The mixed solution was allowed to stand for 1 hour, was then poured over ice, made alkaline with ammonia and extracted with chloroform. The chloroform extract was dried over sodium sulfate and evaporated to dryness in vacuo. The residue, 2-amino-3-bromo-5-carbomethoxy-N,N-diethyl-benzylamine, was dissolved in acetone and its hydrochloride, m.p. 180°–181° C, was precipitated with ethereal hydrochloric acid.

EXAMPLE 32

2-Amino-5-carbomethoxy-N,N-diethyl-benzylamine and its hydrogen fumarate by method C A mixture of 2.5 gm of 2-acetamino-5-carbomethoxy-N,N-diethyl-benzylamine, 50 ml of methanol and 15 ml of concentrated hydrochloric acid was boiled for 30 minutes. The mixture was then poured over ice, made alkaline with ammonia, extracted with chloroform, and the chloroform extract was dried over sodium sulfate and evaporated in vacuo. The residue, 2-amino-5-carbomethoxy-N,N-diethyl-benzylamine, was converted into its hydrogen fumarate, m.p. 177°–179° C, by dissolving it in methanol and adding an ethereal solution of fumaric acid.

EXAMPLE 33

2-Amino-3-bromo-5-carboxy-N-ethyl-benzylamine hydrochloride by method D 2.7 gm of 2-amino-3-bromo-5-carbomethoxy-N-ethylbenzylamine were boiled for 35 minutes with 65 ml of 6 N hydrochloric acid. Thereafter, upon cooling the reaction solution to −15° C, N-ethyl-2-amino-3-bromo-5-carboxy-benzylamine hydrochloride crystallized out and was recrystallized from ethanol/ether, whereupon it had a melting point of 261° C (decomp.).

EXAMPLE 34

2-Amino-5-carboxy-N-(trans-4′-hydroxy-cyclohexyl)-benzylamine hydrochloride, m.p. 224° C (decomp.), was prepared from 2-amino-5-carbethoxy-N-(trans-4′-hydroxy-cyclohexyl)-benzylamine and 6 N hydrochloric acid analogous to Example 33.

EXAMPLE 35

2-Amino-3-bromo-5-carboxy-N-(trans-4′-hydroxy-cyclohexyl)-benzylamine hydrochloride, m.p. 279° C (decomp.), was prepared from 2-amino-3-bromo-5-carbethoxy-N-(trans-4′-hydroxycyclohexyl)-benzylamine and 6 N hydrochloric acid analogous to Example 33.

EXAMPLE 36

2-Amino-5-carboxy-N-(cis-3′-hydroxy-cyclohexyl)-benzylamine dihydrochloride, m.p. 162° C (decomp.), was prepared from 2-amino-5-carbethoxy-N-(cis-3′-hydroxy-cyclohexyl)-benzylamine and 6 N hydrochloric acid analogous to Example 33.

EXAMPLE 37

2-Amino-3-bromo-5-carboxy-N-(cis-3′-hydroxy-cyclohexyl)-benzylamine hydrochloride, m.p. 119° C (decomp.), was prepared from 2-amino-3-bromo-5-carbethoxy-N-(cis-3′-hydroxy-cyclohexyl)-benzylamine and 6 N hydrochloric acid analogous to Example 33.

EXAMPLE 38

2-Amino-5-carbethoxy-N-ethyl-benzylamine and its hydrochloride by method C 3.8 gm of 2-amino-N-benzyl-5-carbethoxy-N-ethyl-benzylamine were hydrogenated in a mixture of 50 ml of methanol and 1 ml of concentrated hydrochloric acid at room temperature and at a hydrogen pressure of 5 atmospheres in the presence of palladized charcoal. Then, the catalyst was filtered off, and the filtrate was evaported to dryness in vacuo. The residue was recrystallized from ethanol by addition of ether, yielding 2-amino-5-carbethoxy-N-ethyl-benzylamine hydrochloride, m.p. 173°–176° C (decomp.).

EXAMPLE 39

3-Bromo-2-butyrylamino-5-carbethoxy-N,N-diethyl-benzylamine and its hydrochloride 3 gm of 2-Amino-3-bromo-5-carbethoxy-N,N-diethylbenzylamine were dissolved in 30 ml of benzene, and the solution was heated for 30 minutes with 3 ml of butyric acid chloride at 50° C. Thereafter, the mixture was evaporated to dryness in vacuo, and the residue was purified by chromatography on silicagel (eluant: benzene/ethyl acetate = 6:1), yielding 3-bromo-2-butyrylamino-5-carbethoxy-N,N-diethylbenzylamine, which was converted into its hydrochloride, m.p. 134° C, with ethanolic hydrochloric acid.

EXAMPLE 40

2-Amino-N-benzyl-5-carbethoxy-N-ethyl-benzylamine and its hydrochloride, m.p. >61° C (decomp.), were prepared from 2-acetamino-5-carbethoxy-benzyl bromide and N-ethylbenzylamine analogous to Example 30 followed by hydrolysis of the crude 2-acetamino-N-ethyl-N-benzyl-5-carbethoxy-benzylamine thus obtained with ethanol/hydrochloric acid analogous to Example 32.

EXAMPLE 41

2-Amino-5-carbethoxy-N-(trans-4'-hydroxy-cyclohexyl)-benzylamine and its hydrochloride, m.p. 237° C (decomp.), were preprared from 2-acetamino-5-carbethoxy-benzyl bromide and trans-4-hydroxy-cyclohexylamine anlogous to Example 30, followed by hydrolysis of the 2-acetamino-5-carbethoxy-N-(trans-4'-hydroxy-cyclohexyl)-benzylamine thus obtained with ethanol/hydrochloric acid analogous to Example 32.

EXAMPLE 42

2-Amino-3-bromo-5-carbethoxy-N-(trans-4'-hydroxy-cyclohexyl)-benzylamine and its hydrochloride, m.p. 137° C (decomp.), were prepared from 2-amino-5-carbethoxy-N-(trans-4'-hydroxycyclohexyl)-benzylamine and bromine analogous to Example 31.

EXAMPLE 43

2-Acetamino-3-bromo-5-carbethoxy-N-cyclohexyl-N-methyl-benzylamine and its hydrochloride, m.p. 220°–223° C, were prepared from 2-amino-3-bromo-5-carbethoxy-N-cyclohexyl-N-methyl-benzylamine and acetyl chloride analogous to Example 39.

EXAMPLE 44

2-Acetamino-N-benzyl-5-carbethoxy-N-tert.butyl-benzylamine and its hydrochloride, m.p. 208° C (decomp.), were prepared from 2-acetamino-5-carbethoxy-benzyl bromide and N-tert.butyl-benzylamine analogous to Example 30.

EXAMPLE 45

2-Amino-5-carbethoxy-N-(cis-3'-hydroxy-cyclohexyl)-benzylamine and its hydrochloride, m.p. 201°–203° C, were prepared from 2-acetamino-5-carbethoxy-benzyl bromide and cis-3-hydroxy-cyclohexylamine analogous to Example 30, followed by hydrolysis of the 2-acetamino-5-carbethoxy-N-(cis-3-hydroxy-cyclohexyl)-benzylamine thus obtained with ethanol/hydrochloric acid analogous to Example 32.

EXAMPLE 46

2-Amino-3-bromo-5-carbethoxy-N-(cis-3'-hydroxy-cyclohexyl)-benzylamine and its hydrochloride, m.p. 103° C (decomp.), were prepared from 2-amino-5-carbethoxy-N-(cis-3-hydroxy-cyclohexyl)-benzylamine and bromine analogous to Example 31.

EXAMPLE 47

2-Amino-5-carbomethoxy-N-(trans-4'-hydroxy-cyclohexyl)-benzylamine and its fumarate, m.p. 221° C (decomp.), were prepared from 2-acetamino-5-carbomethoxy-benzyl bromide and trans-4-hydroxy-cyclohexylamine analogous to Example 30, followed by hydrolysis of the 2-acetamino-5-carbomethoxy-N-(trans-4'-hydroxy-cyclohexyl)-benzylamine thus obtained with methanol/hydrochloric acid analogous to Example 32.

EXAMPLE 48

2-Amino-N,N-diethyl-5-(isopropoxy-carbonyl)-benzylamine and its hydrogen fumarate, m.p. 158° C, were prepared from 2-acetamino-5-(isopropoxy-carbonyl)-benzyl bromide and diethylamine analogous to Example 30, followed by hydrolysis of the 2-acetamino-N,N-diethyl-5-(isopropoxy-carbonyl)-benzylamine thus obtained with isopropanol/hydrochloric acid analogous to Example 32.

EXAMPLE 49

N-Ethyl-2-amino-3-bromo-5-carbethoxy-benzylamine, m.p. 199°–201° C, was prepared from N-ethyl-2-amino-5-carbethoxy-benzylamine and bromine analogous to Example 31.

EXAMPLE 50

2-Amino-3-carboxy-N-cyclohexyl-N-ethyl-benzylamine and its hydrochloride, m.p. 193°–197° C, were prepared from 2-amino-3-carboxy-benzyl bromide and N-ethyl-cyclohexylamine analogous to Example 3.

EXAMPLE 51

2-Amino-5-bromo-3-carboxy-N-cyclohexyl-N-ethyl-benzylamine and its hydrochloride, m.p. 130°–140° C, were prepared from 2-amino-5-bromo-3-carboxy-benzyl bromide and N-ethyl-cyclohexylamine analogous to Example 3.

The compounds embraced by formula I above and their non-toxic pharmacologically acceptable acid addition salts, have useful pharmacodynamic properties. More particularly, the compounds of this invention exhibit anti-ulcerogenic, secretolytic and antitussive activities, as well as a stimulating effect upon the surfactant or antiatelectasis factor of the alveoli in warm-blooded animals, such as guinea pigs, rabbits, rats and cats.

The above-indicated pharmacological activities were ascertained for the compounds of the present invention by the methods described below, and the following are illustrative results obtained for a representative number of compounds, where A = 2-amino-3-bromo-5-carbethoxy-N,N-diethyl-benzylamine hydrochloride, B = 2-amino-3-bromo-5-carboxy-N-cyclohexyl-N-ethyl-benzylamine hydrochloride, 1. Secretolytic Effect The expectorant activity was tested on anesthetized guinea pigs after oral application of 8 mgm/kg of the test compound to 6–8 animals. The increase in secretion within 2 hours was calculated from the amounts of secretion before and after application of the substance [see Perry and Boyd in Pharmakol. exp. Therap. 73, 65 (1941)].

The circulatory effect in cats was determined under chloralose-urethane anesthesia after intravenous application of 2, 4 and 8 mgm/kg of the test compound (3 animals per dose).

Tests in guinea pigs:

| Compound | Increase in secretion | Circulatory effect |
|---|---|---|
| A | +90% | 2, 4 and 8 mgm/kg:no change |
| B | +81% | 2, 4 and 8 mgm/kg:no change |

2. Anti-ulcerogenic activity

The inhibiting effect of the test compounds on the formation of ulcers was determined according to the method of K. Takagi et al. [Jap. J. Pharmac. 19, 418 (1969)]. The abdominal cavity of anesthetized female rats having a body weight from 220 to 250 gm was opened and the stomach was exposed. Then, 0.05 ml of an aqueous 5% acetic acid solution was injected between the muscularis mucosae and submucosa of the stomach. Thereafter, the abdominal cavity was closed again. The ulcers formed in the mucosa after 3 to 5 days were treated for three weeks by admixing the test compound in question with the food at dosage levels of 50 and 100 mgm/kg (6 animals/dose). The control animals were fed with the pulverized food only.

After treatment for three weeks the animals were killed, the stomach was removed, and the size of the ulcers was determined by measurement of their length and width. The anti-ulcerogenic activity of the test compound was determined by the size of the ulcers comparing with the control values (100%):

A peroral dosage of 50 mgm/kg of compound A produced a 52% reduction of the ulcers, and a peroral dosage of 100 mgm/kg produced a 79% reduction of the ulcers, compared with control values.

3. Acute toxicity

The acute toxicity of the test compounds was determined after a single application of 1000 or 2000 mgm/kg p.o., respectively, to 5 white mice each.

| Compound | Acute toxicity |
|---|---|
| A | >2000 mgm/kg p.o. (0 out of 5 animals died) |
| B | >1000 mgm/kg p.o. (0 out of 5 animals died) |

For pharmaceutical purposes the compounds of the formula I or their non-toxic acid addition salts are administered to warm-blooded animals perorally, parenterally or rectally as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups, suppositories and the like.

The single effective dose is from 0.016 to 1.67 mgm/kg, preferably 0.066 to 1.0 mgm/kg body weight. The daily dose rate is 0.032 to 5.0 mgm/kg, preferably 0.064 to 3.3 mgm/kg body weight.

The following examples illustrate a few pharmaceutical compositions comprising a compound of the formula I or a non-toxic acid addition salt thereof as an active ingredient and represent the best modes contemplated of putting the invention to practical use. The parts are parts by weight unless otherwise specified.

EXAMPLE 52

Syrup

The syrup was compounded from the following ingredients:

| | |
|---|---|
| 2-Amino-3-bromo-5-carbethoxy-N,N-diethyl-benzylamine hydrochloride | 0.04 parts |
| Tartaric acid | 0.50 parts |
| Benzoic acid | 0.20 parts |
| Ammonium chloride | 0.40 parts |
| Glycerin | 10.00 parts |
| Sorbitol | 50.00 parts |
| Red food color | 0.01 parts |
| Flavoring | 0.25 parts |
| Ethanol | 10.00 parts |
| Distilled water q.s.ad | 100.00 parts by vol. |

Preparation 45 gm of the distilled water were warmed to 80° C. Then the tartaric acid, the benzoic acid, the benzylamine, the naphthol and the sorbitol were successively dissolved in the water which was subsequently mixed with the glycerin and an aqueous 20% solution of ammonium chloride. After cooling to room temperature, the ethanol and the flavoring were stirred into the mixture. The syrup was diluted to the indicated volume with distilled water and filtered. Each 10 ml portion of the syrup contained 4 mgm of the benzylamine hydrochloride and as an oral dosage unit position with very effective secretolytic, anti-ulcerogenic and antitussive action, as well as a stimulant effect upon the production of the surfactant or antiatelectasis factor of the alveoli.

EXAMPLE 53

Drop Solution

The solution was compounded from the following ingredients:

| | |
|---|---|
| 2-Amino-3-bromo-5-carbethoxy-N,N-diethyl-benzylamine hydrochloride | 0.40 parts |
| p-Hydroxy-benzoic acid methyl ester | 0.07 parts |
| p-Hydroxy-benzoic acid propyl ester | 0.03 parts |
| Polyvinylpyrrolidone | 5.00 parts |
| Anise oil | 0.01 parts |
| Fennel oil | 0.001 parts |
| Ethanol | 10.00 parts |
| Distilled water q.s.ad | 100.00 parts by vol. |

Preparation

The p-hydroxy-benzoic acid esters, the polyvinylpyrrolidone and the benzylamine salt were successively dissolved in the distilled water warmed to 80° C. The solution was cooled and subsequently mixed with the mixture of the aromatic oils and the ethanol. The solution was diluted to the indicated volume with distilled water and filtered. Each ml of drop solution contained 4 mgm of the benzylamine hydrochloride, and was an oral dosage unit composition with very effective secretolytic, anti-ulcerogenic and antitussive action, as well as a stimulant effect upon the production of the surfactant or antiatelectasis factor of the alveoli.

EXAMPLE 54

Tablets

The tablet composition was compounded from the following ingredients:

| | |
|---|---|
| 2-Amino-3-bromo-5-carbethoxy-N,N-diethyl-benzylamine hydrochloride | 4.0 parts |
| Lactose | 60.0 parts |
| Potato starch | 41.0 parts |
| Polyvinylpyrrolidone | 4.0 parts |
| Magnesium stearate | 1.0 parts |
| Total | 110.0 parts |

Preparation

The benzylamine salt was admixed with the lactose and the potato starch and granulated through a screen of 1 mm mesh-size with an aqueous 20% solution of the polyvinylpyrrolidone. The moist granulate was dried at 40° C, again passed through the above mentioned screen and admixed with the magnesium stearate. The mixture was compressed into 110 mgm-tablets. Each tablet contained 4 mgm of the benzylamine salt and was an oral dosage unit composition with very effective secretolytic, anti-ulcerogenic and antitussive action, as well as a stimulant action upon the production of the surfactant or antiatelectasis factor of the alveoli.

EXAMPLE 55

Coated Pills

The pill core composition was compounded from the following ingredients:

| | |
|---|---|
| 2-Amino-3-bromo-5-carbethoxy-N,N-diethyl-benzylamine hydrochloride | 4.0 parts |
| Lactose | 60.0 parts |
| Potato starch | 41.0 parts |
| Polyvinylpyrrolidone | 4.0 parts |
| Magnesium stearate | 1.0 parts |
| Total | 110.0 parts |

Preparation

The benzylamine salt was admixed with the lactose and the potato starch and granulated through a screen of 1 mm mesh-size with an aqueous 20% solution of the polyvinylpyrrolidone. The moist granulate was dried at 40° C, again passed through the above mentioned screen and admixed with the magnesium stearate. The mixture was compressed into 110 mgm-pill cores, which were coated in conventional manner with a thin shell consisting essentially of a mixture of sugar and talcum, and were then polished with beeswax. Each coated pill contained 4 mgm of the benzylamine salt and was an oral dosage unit composition with very effective secretolytic, anti-ulcerogenic and antitussive action, as well as a stimulant effect upon the production of the surfactant or antiatelectasis factor of the alveoli.

EXAMPLE 56

Suppositories

The suppository composition was compounded from the following ingredients:

| | |
|---|---|
| 2-Amino-3-bromo-5-carbethoxy-N,N-diethyl-benzylamine hydrochloride | 4.0 parts |
| Suppository base (e.g. cocoa butter) | 1696.0 parts |
| Total | 1700.0 parts |

Preparation

The finely pulverized benzylamine salt was stirred into the molten suppository base which had been cooled to 40° C, and the mixture was homogenized. 1700 mgm-portions of the mixture were then poured at about 35° C into cooled suppository molds and allowed to harden therein. Each suppository contained 4 mgm of the benzylamine salt and was a rectal dosage unit composition with very effective secretolytic, anti-ulcerogenic and antitussive action, as well as a stimulant effect upon the production of the surfactant or antiatelectasis factor of the alveoli.

EXAMPLE 57

Hypodermic solution

The solution was compounded from the following ingredients:

| | | |
|---|---|---|
| 2-Amino-3-bromo-5-carboxy-N-ethyl-N-cyclohexyl-benzylamine hydrochloride | | 4.0 parts |
| Tartaric acid | | 2.0 parts |
| Glucose | | 95.0 parts |
| Distilled water | q.s.ad | 2000.0 parts by vol. |

Preparation:

Some of the distilled water was warmed to 80° C, and the tartaric acid and the benzylamine salt were dissolved therein while stirring. After cooling to room temperature, the glucose was dissolved therein, the solution was filtered until free from suspended matter, and the filtrate was filled into white 2-ml ampules under aseptic conditions. The filled ampules were then sealed and sterilized at 120° C for 20 minutes. Each ampule contained 4 mgm of the benzylamine salt and was an injectable parenteral dosage unit composition with very effective secretolytic, anti-ulcerogenic and antitussive action, as well as a stimulant effect upon the production of the surfactant or antiatelectasis factor of the alveoli.

Analogous results were obtained when any one of the other compounds embraced by formula I or a non-toxic acid addition salt thereof was substituted for the particular benzylamine salt in Examples 52 through 57. Likewise, the amount of active ingredient in these illustrative examples may be varied to achieve the concentration ranges set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A pharmaceutical dosage unit composition consisting essentially of an inert pharmaceutical carrier and an effective anti-ulcerogenic, secretolytic, antitussive or antiatelectasis factor production stimulating amount of a compound of the formula

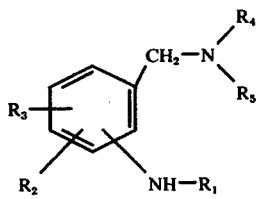

wherein
$R_1$ is hydrogen, lower alkanoyl, benzoyl or halobenzoyl,
$R_2$ is hydrogen, chlorine or bromine,
$R_3$ is carboxyl or lower carbalkoxy, and
$R_4$ and $R_5$ are each hydrogen, alkyl of 1 to 5 carbon atoms, mono- or di-hydroxy-(alkyl of 1 to 5 carbon atoms), alkenyl of 2 to 4 carbon atoms, cycloalkyl of 5 to 7 carbon atoms, mono- or di-hydroxy-(cycloalkyl of 5 to 7 carbon atoms) or benzyl,
or a non-toxic, pharmacologically acceptable acid addition salt thereof.

2. A composition of claim 1, where said compound is 2-amino-3-bromo-5-carbethoxy-N,N-diethyl-benzylamine or a non-toxic, pharmacologically acceptable acid addition salt thereof.

3. A composition of claim 1, where said compound is 2-amino-3-bromo-5-carboxy-N-cyclohexyl-N-ethyl-benzylamine or a non-toxic pharmacologically acceptable acid addition salt thereof.

4. The method of stimulating the secretion of respiratory fluids, suppressing coughs, preventing ulcers or stimulating the production of the antiatelectasis factor of the alveoli in a warm-blooded animal, which comprises perorally, parenterally or rectally administering to said animal an effective secretolytic, antitussive, anti-ulcerogenic or antiatelectasis factor production stimulating amount of a compound of the formula

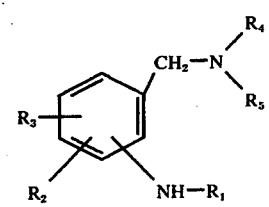

wherein
$R_1$ is hydrogen, lower alkanoyl, benzoyl or halobenzoyl,
$R_2$ is hydrogen, chlorine or bromine,
$R_3$ is carboxyl or lower carbalkoxy, and
$R_4$ and $R_5$ are each hydrogen, alkyl of 1 to 5 carbon atoms, mono- or di-hydroxy-(alkyl of 1 to 5 carbon atoms), alkenyl of 2 to 4 carbon atoms, cycloalkyl of 5 to 7 carbon atoms, mono- or di-hydroxy-(cycloalkyl of 5 to 7 carbon atoms) or benzyl,
or a non-toxic, pharmacologically acceptable acid addition salt thereof.

5. The method of claim 4, where said compound is 2-amino-3-bromo-5-carbethoxy-N,N-diethyl-benzylamine or a non-toxic, pharmacologically acceptable acid addition salt thereof.

6. The method of claim 4, where said compound is 2-amino-3-bromo-5-carboxy-N-cyclohexyl-N-ethyl-benzylamine or a non-toxic, pharmacologically acceptable acid addition salt thereof.

* * * * *